United States Patent
Joshi et al.

(10) Patent No.: US 7,512,209 B2
(45) Date of Patent: Mar. 31, 2009

(54) THERMAL STABILIZATION METHODS AND APPARATUS

(75) Inventors: Ashutosh Joshi, Waukesha, WI (US); Joseph James Lacey, Cambridge, WI (US)

(73) Assignee: General Electric Company, Schenectedy, NY (US)

( * ) Notice: Subject to any disclaimer, the term of this patent is extended or adjusted under 35 U.S.C. 154(b) by 42 days.

(21) Appl. No.: 11/521,029

(22) Filed: Sep. 14, 2006

(65) Prior Publication Data

US 2008/0069296 A1    Mar. 20, 2008

(51) Int. Cl.
    *H05G 1/64*    (2006.01)
(52) U.S. Cl. .................... 378/19; 378/98.8; 378/117
(58) Field of Classification Search ............ 378/19, 378/98.8, 117
    See application file for complete search history.

(56) References Cited

U.S. PATENT DOCUMENTS

| 4,503,327 | A  | * | 3/1985  | Wilson .................... 250/261    |
| 4,535,780 | A  |   | 8/1985  | Gur et al. .................. 128/659  |
| 4,831,639 | A  | * | 5/1989  | Harke ........................ 378/19  |
| 4,991,193 | A  |   | 2/1991  | Cecil et al. ................. 378/117 |
| 5,006,425 | A  |   | 4/1991  | Takabayashi ................ 429/23    |
| 5,138,642 | A  |   | 8/1992  | McCroskey et al. .......... 378/19     |
| 5,444,752 | A  | * | 8/1995  | Dobbs et al. ................. 378/19  |
| 5,521,387 | A  | * | 5/1996  | Riedner et al. .............. 250/367  |
| 5,596,228 | A  | * | 1/1997  | Anderton et al. ............ 257/714   |
| 6,249,563 | B1 | * | 6/2001  | Snyder et al. ................. 378/19 |
| 6,420,711 | B2 | * | 7/2002  | Tumer ................... 250/370.09   |
| 6,621,084 | B1 | * | 9/2003  | Wainer et al. ........... 250/370.09   |
| 6,658,082 | B2 | * | 12/2003 | Okumura et al. ............. 378/19    |
| 7,062,016 | B2 |   | 6/2006  | Kawabuchi ................ 378/118     |
| 7,135,687 | B2 | * | 11/2006 | Lacey et al. ............ 250/370.15   |
| 2004/0022351 | A1 | * | 2/2004 | Lacey et al. .................. 378/19 |

* cited by examiner

*Primary Examiner*—Edward J Glick
*Assistant Examiner*—Thomas R Artman
(74) *Attorney, Agent, or Firm*—Fisher Patent Group, LLC; Thomas M. Fisher

(57) ABSTRACT

A method includes thermally stabilizing a Computed Tomography (CT) detector module.

9 Claims, 3 Drawing Sheets

THERMAL STABILIZATION METHODS AND APPARATUS

BACKGROUND OF THE INVENTION

This invention relates generally to methods and apparatus for computed tomography (CT), and more particularly to methods and apparatus for thermal stabilization for x-ray detectors in CT.

Present day CT systems use multi-slice detectors and data acquisition electronics connected/attached to detector modules. The scanner is required to operate for very low and high room temperature conditions. The data acquisition electronics generate heat and are cooled by forced air using axial flow fans. The detector modules temperatures are controlled by controlling the temperature of metallic rails using flexible heaters and variable speed fans. Thermal stability of the detector modules is critical to image quality. There is a requirement of CT detectors to operate at very high gantry speeds. Thermal stability of detector modules is important at high-speed gantry operations due to wind-effect on rails and fan efficiency degradation. The thermal stability of detector modules is important during the x-ray data and calibration to keep the calibration conditions updated.

BRIEF DESCRIPTION OF THE INVENTION

In one aspect, a method includes thermally stabilizing a Computed Tomography (CT) detector module.

In another aspect, a computed tomography (CT) system includes a radiation source configured to emit radiation, a detector positioned to receive the radiation, and a thermal stabilization system operationally coupled to said detector.

In yet another aspect, an x-ray detector includes a scintillator layer configured to convert x-rays to photons of less energy, a photodiode layer positioned to receive photons emitted from the scintillator layer, a analog to digital (A/D) device operationally coupled to the photodiode layer, and a thermal stabilization system operationally coupled to said photodiode layer and said A/D device.

In still yet another aspect, a product line of computed tomography (CT) systems is provided. The product line includes a first CT system including a first radiation source configured to emit radiation, a first detector positioned to receive the radiation, and a first thermal stabilization system operationally coupled to the first detector. The product line also includes a second CT system including a second radiation source configured to emit radiation, a second detector positioned to receive the radiation, and a second thermal stabilization system operationally coupled to the second detector. Wherein the second thermal stabilization system has a heat dispersion capacity different than the first thermal stabilization system, and the first and second detectors and sources are substantially identical.

DETAILED DESCRIPTION OF THE INVENTION

Figure 1:
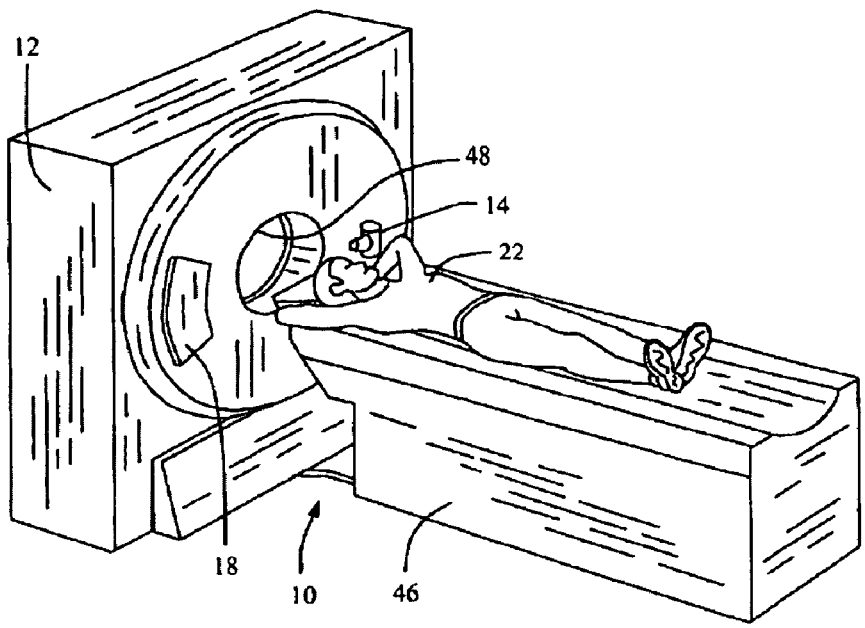
FIG. 1 is a pictorial view of a CT imaging system embodiment.

There are herein provided methods and apparatus useful for imaging systems such as, for example, but not limited to a Computed Tomography (CT) System. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention. This disclosure presents temperature stabilization methods and apparatus for CT detector modules for high-speed applications.

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to reconstruct an image that corresponds to a two-dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display device.

To reduce the total scan time, a "helical" scan may be performed. To perform a "helical" scan, the patient is moved on table axially while the data for the prescribed number of slices is acquired. Such a system generates a single helix from a cone beam helical scan. The helix mapped out by the cone beam yields projection data from which images in each prescribed slice may be reconstructed.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Figure 2:
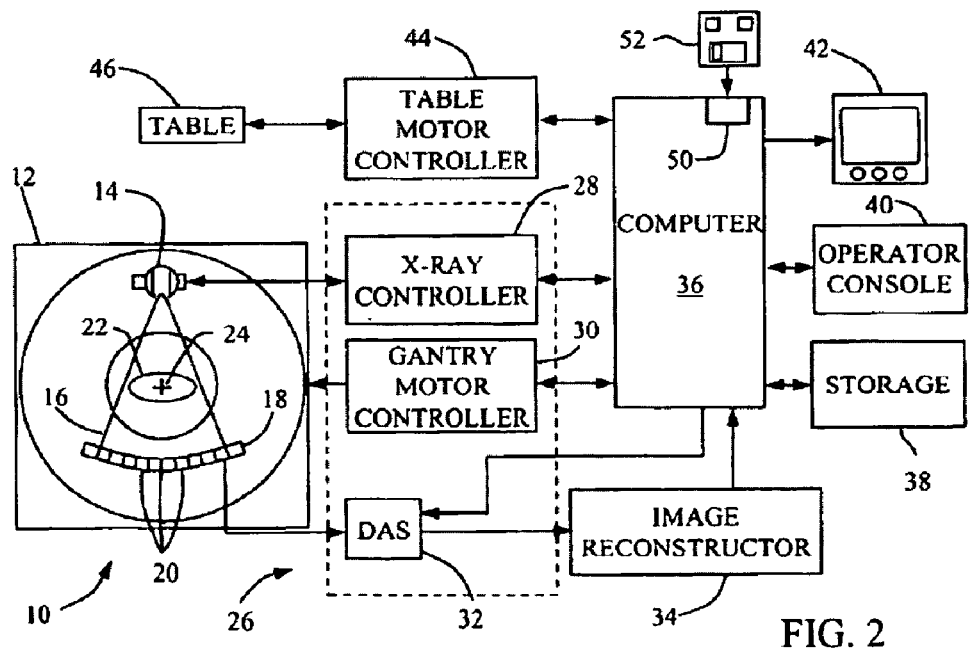
FIG. 2 is a block schematic diagram of the system illustrated in FIG. 1.

FIG. 1 is a pictorial view of a CT imaging system 10. FIG. 2 is a block schematic diagram of system 10 illustrated in FIG. 1. In the exemplary embodiment, a computed tomography (CT) imaging system 10, is shown as including a gantry 12 representative of a "third generation" CT imaging system. Gantry 12 has a radiation source 14 that projects a beam 16 of X-rays toward a detector array 18 on the opposite side of gantry 12.

Detector array 18 is formed by a plurality of detector rows (not shown in FIGS. 1 and 2) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 that stores the image in a mass storage device 38.

Computer 36 also receives commands and scanning parameters from an operator via a console 40 that has a keyboard. An associated cathode ray tube display 42 allows the operator to observe the reconstructed image and other data from computer 36. The operator supplied commands and parameters are used by computer 36 to provide control signals and information to DAS 32, radiation controller 28, and gantry motor controller 30. In addition, computer 36 operates a table motor controller 44 that controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital means. In another embodiment, computer 36 executes instructions stored in firmware (not shown). Generally, a processor in at least one of DAS 32, reconstructor 34, and computer 36 shown in FIG. 2 is programmed to execute the processes described below. Of course, the method is not limited to practice in CT system 10 and can be utilized in connection with many other types and variations of imaging systems. In one embodiment, Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits.

Although the herein described methods are described in a medical setting, it is contemplated that the benefits of the invention accrue to non-medical imaging systems such as those systems typically employed in an industrial setting or a transportation setting, such as, for example, but not limited to, a baggage scanning CT system for an airport or other transportation center. Additionally, although described in a human patient setting it is contemplated that the benefits of the invention accrue to non-human imaging systems such as those used to image animals.

Returning now to the topic of temperature stabilization methods and apparatus for CT detector modules for high-speed applications. The present generation CT detector consists of detector modules that convert the x-rays into electrical signal using scintillators and photodiodes. The scintillators convert the x-rays to photons of lesser energy that impinge and charge the photodiodes. Both of these devices (scintillators and photodiodes) are sensitive to temperature change. There is an electronics circuit to convert the analog electrical signals into digital signals using analog to digital (A/D) devices. The electrical requirements are such that the A/Ds are required to be in very close proximity to the detection device. High-speed gantry rotation is required for some of the advanced procedures using CT system. The heat load of the A/D circuit required is quite low due to close proximity of the processing circuit and detection device. Herein described are methods and apparatus for providing thermal stability of such detector devices that has A/D chips mounted very close to the photodiodes and scintillators.

Figure 3:
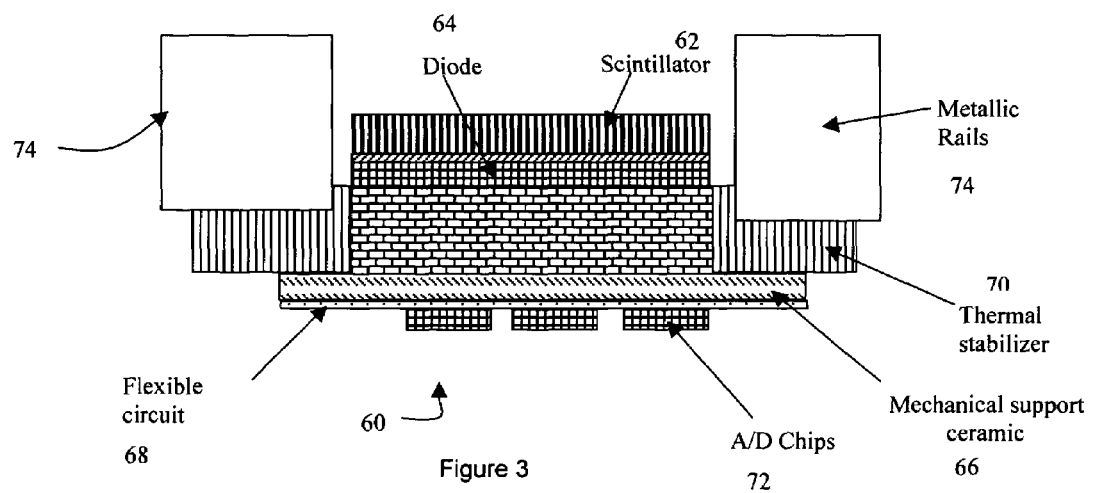
FIG. 3 illustrates one embodiment of an x-ray detector.
Figure 4:
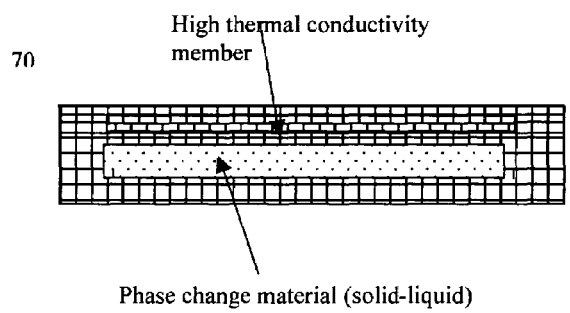
FIG. 4 illustrates the eutectic embodiment.
Figure 5:
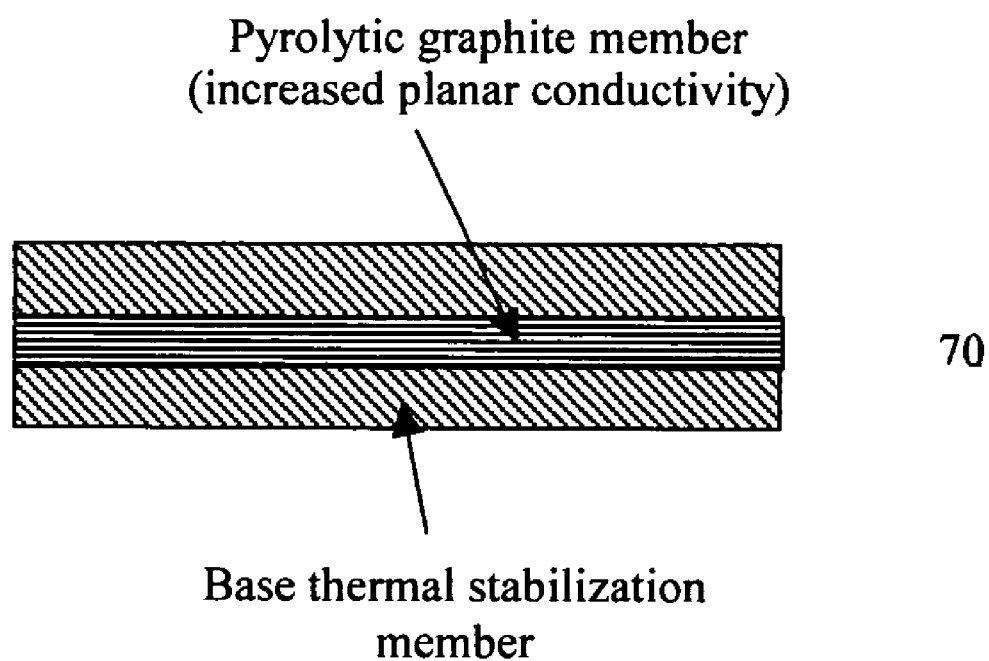
FIG. 5 illustrates that another alternative is to provide a sandwich of high conductivity pyrolytic graphite between two layers of high conductivity metal/ceramic.

FIG. 3 illustrates one embodiment of an x-ray detector 60 including a scintillator layer 62 and a photodiode layer 64. One embodiment uses a ceramic member as a mechanical support 66, which has higher thermal conductivity on which multiple A/Ds 72 are mounted on a flexible circuit 68. Collectively, FIGS. 3-5 illustrate different components that in different combinations form different thermal stabilization systems. Additionally, although not shown in the drawings, one embodiment employs temperature sensors, and if/when the thermal stabilization system should fail, a notification is made to the user to obtain a service call. In another embodiment, the service call is made automatically when a malfunction is detected. The temperature sensors in combination with a networked environment, allow for remote diagnostics of the thermal stabilization system.

The substrate is mechanically mounted on a thermal stabilizer member that is connected to metallic rails 74. Flexible circuit 68 is connected to another ceramic substrate on which diodes 64 are electrically mounted. The thermal stabilizer member 70 is sandwiched between the first mechanical ceramic and second electrical ceramic substrate. Thermal stabilizer member 70 can be made of material of high thermal conductivity, high density, and high specific heat. Thermal stabilizer member 70 may have a tailorable CTE (Coefficient of Thermal expansion) so that thermal mismatch between different parts is minimized to reduce the stress on the electronics. Thermal conductivity of the member is required to be higher than 200 W/m-K and the thermal mass (density×specific heat) is high enough to have slow changes in temperature during gantry rotation and scanning to achieve artifact free images. So thermal mass could be enhanced by increasing the product of density and specific heat to achieve slow temperature change of diode and scintillator during scan time window.

The thermal member 70 may be made of copper-Tungsten, Copper-Molybdenum-Tungsten, or other similar alloys, which has high thermal conductivity, and mass which makes the heat to transfer from the electronics and stabilize. In addition, one can connect this high thermal conductivity member 70 to the metallic rails 74, which are used as heat sinks during the detector operation.

As an alternative, the thermal stabilization member 70 may have a circular or rectangular cavity on which a super thermal conductor such as a heat pipe is attached which makes thermal transfer even more efficient.

During the high-speed rotation of the CT gantry, air temperature and speed variation would affect the thermal performance of the detector module. In this disclosure, we have a thermal member with one rectangular or circular cavity filled with a material that has solid to liquid phase transition to help thermal stabilization of the module. In other words, one embodiment makes use of a eutectic phase change material that has a large heat capacity while undergoing a phase change. In one embodiment, the eutectic phase change material has a tailorable melting point. FIG. 4 illustrates the eutectic embodiment. The temperature of the phase transition is customized (using different additives) depending on the temperature requirements for the detector module.

FIG. 5 illustrates that another alternative is to provide a sandwich of high conductivity pyrolytic graphite between two layers of high conductivity metal-alloy to increase the planar thermal conductivity of the member that ensures that there is smaller temperature gradient along the patient axis. This gradient should be small enough (0.02 deg C./mm along patient axis of the detector module) to maintain the smallest change in thermal profile for the whole detector from calibration to imaging, especially the center modules of the detector which are important for CT image quality.

Technical effects of the herein described methods and apparatus include that the detector module is thermally stable during high-speed gantry rotation scanning of a patient and calibration of the scanner. In addition, the herein described methods and apparatus ensure that the thermal gradient along the patient axis is minimum and that is important for next generation detector modules. The herein described methods and apparatus also ensure that the parts do not see thermal mismatch and will experience lower thermo-mechanical stresses.

Another technical effect is lower thermo-mechanical stress on the detector modules. The herein described methods and apparatus also provide temperature control for advanced energy discrimination CT detectors.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. A method useful with a Computed Tomography (CT) system, said method comprising:
at least partially thermally stabilizing a Computed Tomography (CT) detector module by providing a eutectic material to absorb heat; and
at least partially thermally stabilizing the CT detector module by by providing a sandwich of pyrolytic graphite between two layers of metal alloy to thermally stabilize the CT detector module, such that the sandwich is between a support rail and a photodiode layer of the detector module, wherein the sandwich is a heat pipe that aids the eutectic material such that together the sandwich and the eutectic material thermally stabilizes the CT detector module by transferring heat and absorbing heat.

2. A method in accordance with claim 1 wherein the sandwich and eutectic material have a combined thermal conductivity of at least 200 W/m-K.

3. A method in accordance with claim 1 further comprising using a metallic rail as a heat sink to thermally stabilize the CT detector module.

4. An x-ray detector comprising:
a scintillator layer configured to convert x-rays to photons of less energy;
a photodiode layer positioned to receive photons emitted from said scintillator layer;
a analog to digital (A/D) device operationally coupled to said photodiode layer; and
a thermal stabilization system operationally coupled to said photodiode layer and said A/D device, wherein said thermal stabilization system comprises a eutectic material and a sandwich of pyrolytic graphite between two layers of metal alloy, wherein the thermal stabilization system is mounted to a rail and connects the rail to the photodiode layer.

5. A detector in accordance with claim 4 wherein said thermal stabilization system comprises a heat pipe.

6. A detector in accordance with claim 4 wherein said thermal stabilization system comprises a metallic rail.

7. A product line of computed tomography (CT) systems, said product line comprising:
a first CT system comprising:
a first radiation source configured to emit radiation;
a first detector positioned to receive the radiation; and
a first thermal stabilization system operationally coupled to said first detector; and
a second CT system comprising:
a second radiation source configured to emit radiation;
a second detector positioned to receive the radiation; and
a second thermal stabilization system operationally coupled to said second detector, wherein said second thermal stabilization system has a heat dispersion capacity different than said first thermal stabilization system and said first and second detectors and sources are substantially identical.

8. A product line in accordance with claim 7 wherein said first and said second thermal stabilization systems comprise eutectic material with different melting points.

9. A product line in accordance with claim 7 wherein said first and said second thermal stabilization systems comprise different thermal masses.

* * * * *